(12) United States Patent
Ma

(10) Patent No.: US 8,607,799 B1
(45) Date of Patent: Dec. 17, 2013

(54) MALE CHASTITY DEVICE

(71) Applicant: Youxian Ma, Handan (CN)

(72) Inventor: Youxian Ma, Handan (CN)

( * ) Notice: Subject to any disclaimer, the term of this patent is extended or adjusted under 35 U.S.C. 154(b) by 0 days.

(21) Appl. No.: 13/858,945

(22) Filed: Apr. 9, 2013

(51) Int. Cl.
*A61F 5/37* (2006.01)
*A61F 5/00* (2006.01)

(52) U.S. Cl.
USPC ............................................ 128/883; 600/41

(58) Field of Classification Search
USPC ................ 600/38, 39, 41; 602/67, 68, 72; 119/712, 814, 838; 128/883, 869, 846
See application file for complete search history.

(56) References Cited

U.S. PATENT DOCUMENTS

| | | |
|---|---|---|
| 5,370,130 A | 12/1994 | Hess |
| 5,370,131 A | 12/1994 | Hess |
| 7,578,296 B2 | 8/2009 | Miller et al. |
| 8,007,431 B2 * | 8/2011 | Miller et al. ............ 600/39 |

* cited by examiner

*Primary Examiner* — Patricia Bianco
*Assistant Examiner* — Tarla Patel
(74) *Attorney, Agent, or Firm* — Michael D. Eisenberg

(57) ABSTRACT

A male chastity comprises a first loop, a cup, a second loop hinged to the first loop and optionally to the cup, and a removable fixing mechanism. The first loop is configured for being traversed by the user's penis and scrotum, and for encircling the penis behind the scrotum. The second loop is configured for being traversed by at least the penis, and for encircling the penis ahead of the scrotum, so that the user's testicles are located between the first loop and second loop. The cup is configured for enclosing at least a head of the penis. The removable fixing mechanism is configured, when joined to the device, for preventing removal of the device form the penis by limiting or blocking relative rotation between the first loop and the second loop, and, if needed, by limiting or blocking relative rotation between the cup and the second loop.

17 Claims, 12 Drawing Sheets

MALE CHASTITY DEVICE

TECHNICAL FIELD

The present invention, relates to chastity device, and more particularly with male chastity devices.

BACKGROUND OF THE INVENTION

Chastity devices have a long and varied history. Female chastity devices are generally easier to conceive and produce, as their aim is to prevent penetration and their shape is designed to match the simple female external anatomy. Male chastity devices are harder to produce, given the more complex external anatomy of the male reproductive system.

Generally, male chastity device enclose a male user's penis, and may be locked by a key held by the user's partner or guardian, to ensure that the user does not perform sexual acts. Such a device is described, for example, in U.S. Pat. Nos. 7,578,296 and 8,007,431.

U.S. Pat. Nos. 7,578,296 and 8,007,431 disclose a male chastity system which comprises a housing and a partial ring configured for placement behind the scrotum of the user. The partial ring contains a gap. A bridge bridges the gap by attaching to the partial ring at first and second attachment points. The bridge comprises a rear portion and a front portion, and the partial ring and the bridge collectively form a ring. Guide pins extend at least partially through the rear bridge portion, attachment points, front bridge portion, and housing. A locking pin extends through the bridge and housing, a spacer on the locking pin spacing the housing from the ring, and a lock is applied to the locking pin.

BRIEF SUMMARY OF EMBODIMENTS OF THE INVENTION

In the prior art, the whole penis is enclosed within a housing. This may constrain the motion of the penis and cause discomfort to the user, while the housing may make the chastity device uncomfortably heavy. Friction between the penis and housing may make it difficult to insert the penis within the housing. Moreover, the fixed size of the device may not fit the size of the user's penis, causing the penis to crumple within the housing or at the opening of the housing.

To decrease these discomforts, some products of the prior art come with instructions which advise the user to user lubrication while attempting to wear the device. However, the application of the lubrication may be a step that would inconvenience the user. One solution for avoiding the above-mentioned discomforts may be to enlarge the housing, thus reducing friction and enabling the entire penis to be held in the housing without crumpling. However, an enlarged housing may cause the device to be easily noticed under the user's clothing, thus causing some embarrassment to the user and the people around him.

The present invention is aimed at a chastity device designed for preventing sexual intercourse of the user, without enclosing the whole penis, thus enhancing the comfort of the device and decreasing the device's weight. Because the penis is not entirely enclosed, circulation, dryness and comfort are maintained. Moreover, because the penis is not entirely enclosed, the need for applying a lubricant to the penis is obviated.

Therefore, an aspect of some embodiments of the present invention relates to a male chastity device, comprising a first loop, a second loop, a cup, a first hinging unit, and a removable fixing mechanism. The first loop is configured for being traversed by a penis and scrotum of a user, and for encircling the penis behind the scrotum. The second loop is configured for being traversed by at least the penis, and for encircling the penis ahead of the scrotum, so that the user's testicles are located between the first loop and second loop. The cup is joined to the second loop and configured for enclosing at least a head of the penis. The first hinging unit joins the first loop to the second loop, and enables the first and second loop to rotate with respect to each other. The removable fixing mechanism is configured for being removably joined to the device and, when joined to the device, for preventing removal of the device from the penis by limiting or blocking relative rotation between the first loop and the second loop.

In a variant, the cup and the second loop are not movable with respect to each other.

In another variant, the cup and the second loop are rotatable with respect to each other. The device comprises a second hinging unit, joining the second loop to the cup, and enabling the cup and second loop to rotate with respect to each other. The removable fixing mechanism, when joined to the device, is configured for preventing removal of the device from the penis by limiting or blocking relative rotation between the first loop and the second loop, and by limiting or blocking relative rotation between the cup and the second loop.

In yet another variant, the device comprises a removable locking mechanism, configured for being removably joined to the fixing mechanism to prevent a removal of the fixing mechanism from the device, and removed from the fixing mechanism to enable a removal of the fixing mechanism from the device.

In a further variant, the first hinging unit comprises: a first appendage joined to the first loop and extending away from a plane of the first loop, the first appendage having a first aperture; a second appendage joined to the second loop and extending away from a plane of the second loop, the second appendage having a second aperture; and a first pin configured for traversing the first and second apertures, thereby joining the first loop and the second loop, while enabling the first and second loop to rotate with respect to each other about the first pin.

Optionally, the first hinging unit further comprises: a third appendage joined to the first loop and extending away from a plane of the first loop, the third appendage being substantially parallel to the first appendage and having a third aperture; a fourth appendage joined to the second loop and extending away from a plane of the second loop, the fourth appendage having a fourth aperture; and a second pin configured for traversing the third and fourth apertures, thereby joining the first loop and the second loop. The first, second, third, and fourth apertures are aligned along a first axis when the first and second loops are joined, such that the first and second pins are aligned to extend along the first axis, thereby enabling the first and second loop to rotate with respect to each other.

In yet a further variant, the second loop has a fifth aperture, and the second hinging unit comprises: a fifth appendage joined to the cup, extending away from the cup on the cup's concave side, and having a sixth aperture; and a third pin configured for traversing the fifth aperture and the sixth aperture thereby joining the cup and the second loop, while enabling the cup and second loop to rotate with respect to each other.

Optionally, the second loop has a seventh aperture and the second hinging unit further comprises: a sixth appendage joined to the cup, extending away from the cup on the cup's concave side, and having an eighth aperture; and a fourth pin configured for traversing the seventh and eighth apertures thereby joining the cup and the second loop. The fifth, sixth, seventh, and eighth apertures are aligned along a second axis when the cup and the second loop are joined, such that the third and fourth pins are aligned to extend along the second axis, thereby enabling the cup and the second loop to rotate with respect to each other.

In some embodiments of the present invention, the first appendage has a first hole and the second appendage has a second hole. The fixing mechanism comprises a first peg configured for traversing the first and second holes when the first and second holes are aligned with each other, thereby limiting the relative rotation between the first loop and the second loop about the first pin.

In a variant, the first appendage has a first hole and the second appendage has a second hole. The third appendage has a third hole and the fourth appendage has a fourth hole. The fixing mechanism comprises a first peg and a second peg. The first peg is configured for traversing the first and second holes when the first and second holes are aligned with each other, thereby limiting the relative rotation between the first loop and the second loop about the first pin. The second peg is configured for traversing the third and fourth holes when the third and fourth holes are aligned with each other, thereby limiting the relative rotation between the first loop and the second loop about the second pin.

In another variant, the device comprises a first tube joined to the second loop, wherein the fixing mechanism comprises a third peg configured for traversing the first tube and for pressing on an outer surface of the cup for preventing the relative rotation between the cup and second loop.

In yet another variant, the device comprises a second tube joined to the outer surface of the cup, wherein the third peg is configured for traversing the first tube and the second tube when the first and second tubes are aligned with each other, thereby for preventing the relative rotation between the cup and second loop.

In a further variant, the device comprises a first tube joined to the second loop. The cup and the second loop are rotatable with respect to each other. The device comprises a second hinging unit, joining the second loop to the cup, and enabling the cup and second loop to rotate with respect to each other. The removable fixing mechanism, when joined to the device, is configured for preventing removal of the device from the penis by limiting or blocking relative rotation between the first loop and the second loop, and by limiting or blocking relative rotation between the cup and the second loop. The fixing mechanism further comprises a third peg configured for traversing the first tube and for pressing on an outer surface of the cup for preventing the relative rotation between the cup and second loop. The first peg comprises a first rod configured for traversing the first and second holes and a first bar joined to the first rod and oriented at a non-zero angle with respect to the first rod, the first bar having a first orifice. The third peg has a third orifice. The device is configured such that the first orifice and the third orifice are aligned along a third axis when the first peg traverses the first and second holes and the third peg traverses the first tube and presses on the cup's outer surface.

In yet a further variant, the device comprises a first tube joined to the second loop. The first peg comprises a first rod configured for traversing the first and second holes and a first bar joined to the first rod and oriented at a non-zero angle with respect to the first rod, the first bar having a first orifice. The second peg comprises a second rod configured for traversing the third and fourth holes and a second bar joined to the second rod and oriented at a non-zero angle with respect to the second rod, the second bar having a second orifice. The device is configured such that the first orifice, the second orifice, and the third orifice are aligned along a third axis when the first peg traverses in the first and second holes, the second peg traverses the third and fourth holes.

According to some embodiments of the present invention, the device comprises a first tube joined to the second loop. The cup and the second loop are rotatable with respect to each other. The device comprises a second hinging unit, joining the second loop to the cup, and enabling the cup and second loop to rotate with respect to each other. The removable fixing mechanism, when joined to the device, is configured for preventing removal of the device from the penis by limiting or blocking relative rotation between the first loop and the second loop, and by limiting or blocking relative rotation between the cup and the second loop. The fixing mechanism further comprises a third peg configured for traversing the first tube and for pressing on an outer surface of the cup for preventing the relative rotation between the cup and second loop. The first peg comprises a first rod configured for traversing the first and second holes and a first bar joined to the first rod and oriented at a non-zero angle with respect to the first rod, the first bar having a first orifice. The second peg comprises a second rod configured for traversing the third and fourth holes and a second bar joined to the second rod and oriented at a non-zero angle with respect to the second rod, the second bar having a second orifice. The third peg has a third orifice. The device is configured such that the first orifice, the second orifice, and the third orifice are aligned along a third axis when the first peg traverses the first and second holes, the second peg traverses the third and fourth holes, and the third peg traverses the first tube and presses on the cup's outer surface.

In a variant, the device comprises a padlock having a shackle and a body, wherein the shackle is configured for traversing the first and third orifices when the first and third orifices are aligned along the third axis and for being locked to the body, to prevent a removal of the first and third pegs, thereby preventing removal of the fixing mechanism and removal of the device from the penis.

In another variant, the device comprises a padlock having a shackle and a body, wherein the shackle is configured for traversing the first and second orifices when the first and second orifices are aligned along the third axis and for being locked to the body, to prevent a removal of the first and second pegs, thereby preventing removal of the fixing mechanism and removal of the device from the penis.

In yet another variant, the device comprises a padlock having a shackle and a body, wherein the shackle is configured for traversing the first, second, and third orifices when the first, second, and third orifices are aligned along the third axis and for being locked to the body, to prevent a removal of the first, second, and third pegs, thereby preventing removal of the fixing mechanism and removal of the device from the penis.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

Figure 1:
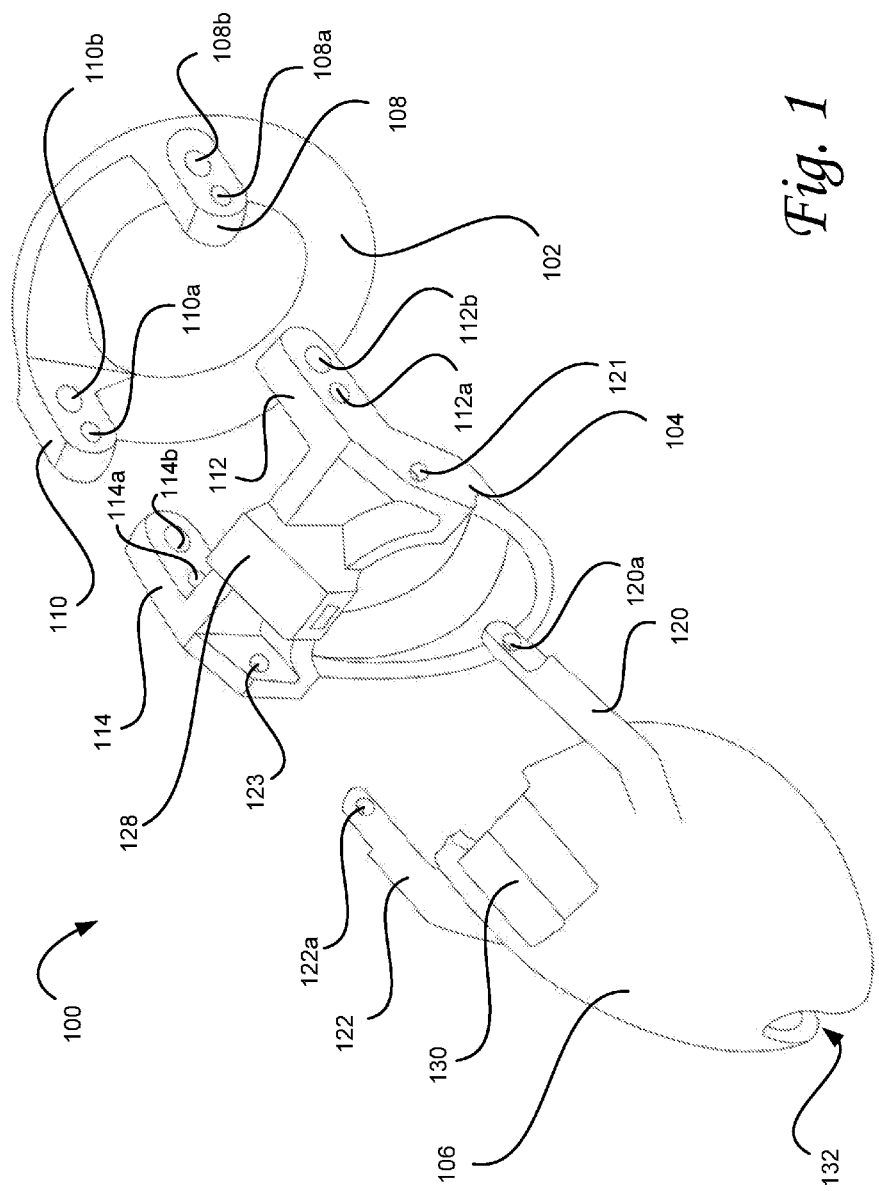
FIG. 1 is a perspective drawing illustrating a first loop, a second loop, and a cup of the device of the present invention detached from each other.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Before referring to the drawings, a glossary is presented to indicate elements that will be discusses below along with their respective reference numerals:

100 male chastity device
102 first loop
104 second loop
106 cup
108 first appendage
108a first hole
108b first aperture
110 second appendage
110a second hole
110b second aperture
112 third appendage
112a third hole
112b third aperture
114 fourth appendage
114a forth hole
114b forth aperture
116 first pin
118 second pin
120 fifth appendage
120a fifth aperture
121 aperture
122 sixth appendage
122a sixth aperture
123 aperture
124 third pin
126 forth pin
128 first tube
130 second tube
132 slit
200 penis shaft
201 testicle
202 scrotum
204 penis head
300 first two-part peg
302 second two-part peg
304 straight peg
306 first rod
308 first bar
310 first orifice
312 second rod
314 second bar
316 second orifice
318 third orifice
320 bar section of 304
322 rod section of 304
324 axis
400 padlock
402 shackle
404 body of padlock.

Figure 2:
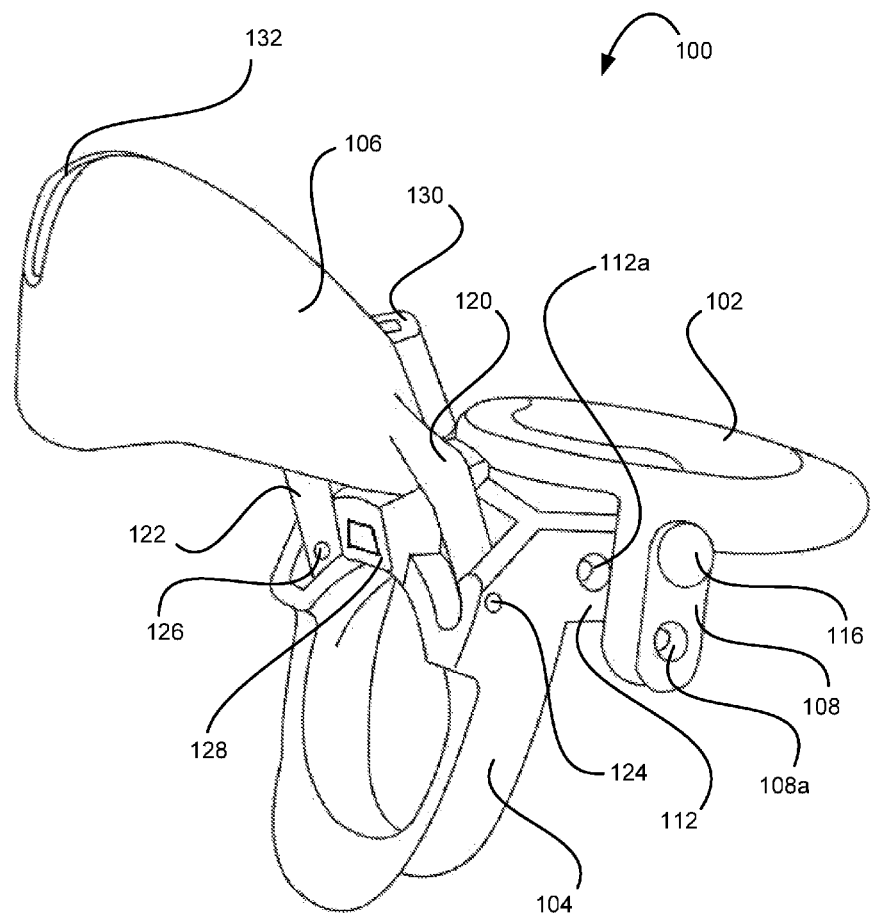
FIG. 2 is a perspective drawing illustrating a device of the present invention in an open mode.
Figure 3:
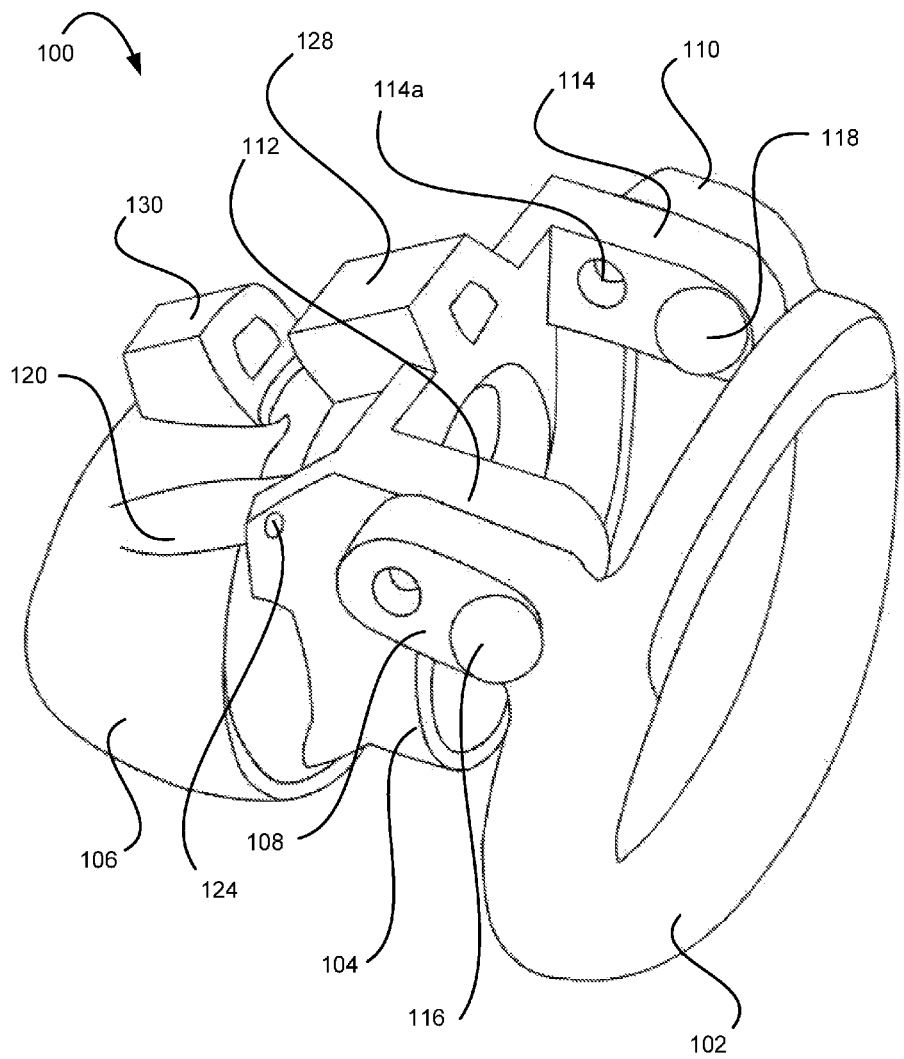
FIGS. 3 and 4 are perspective drawings illustrating a device of the present invention in a closed mode.
Figure 4:
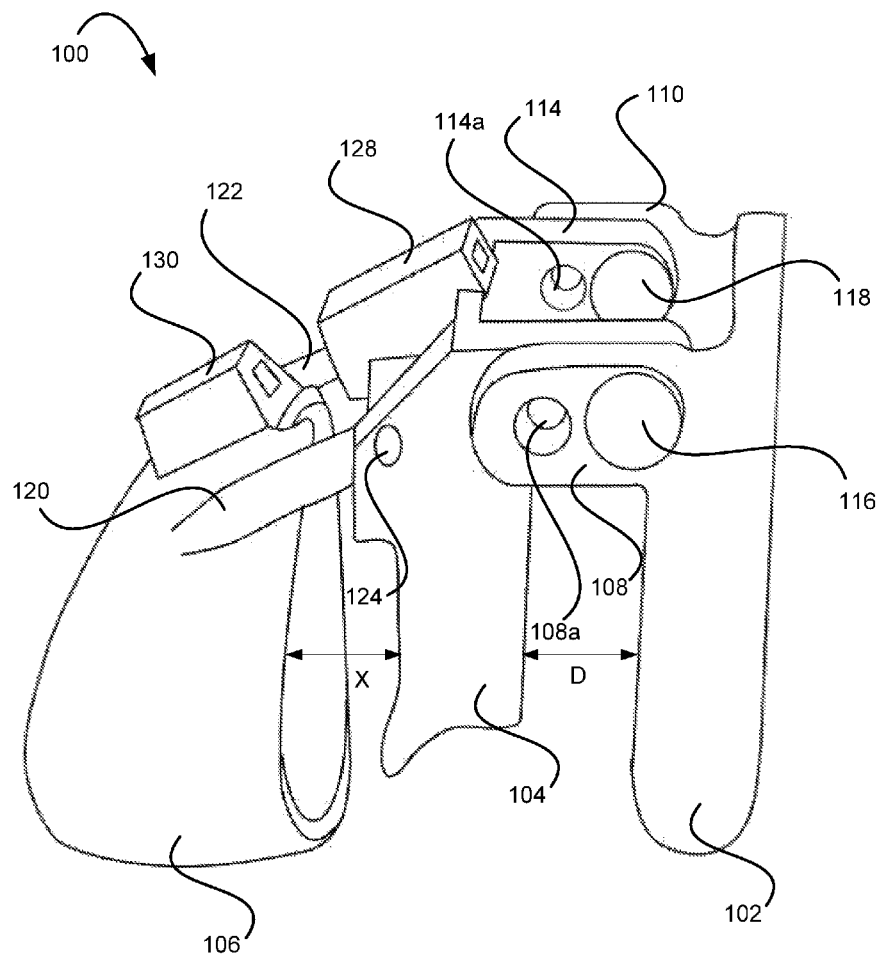
Figure 5:
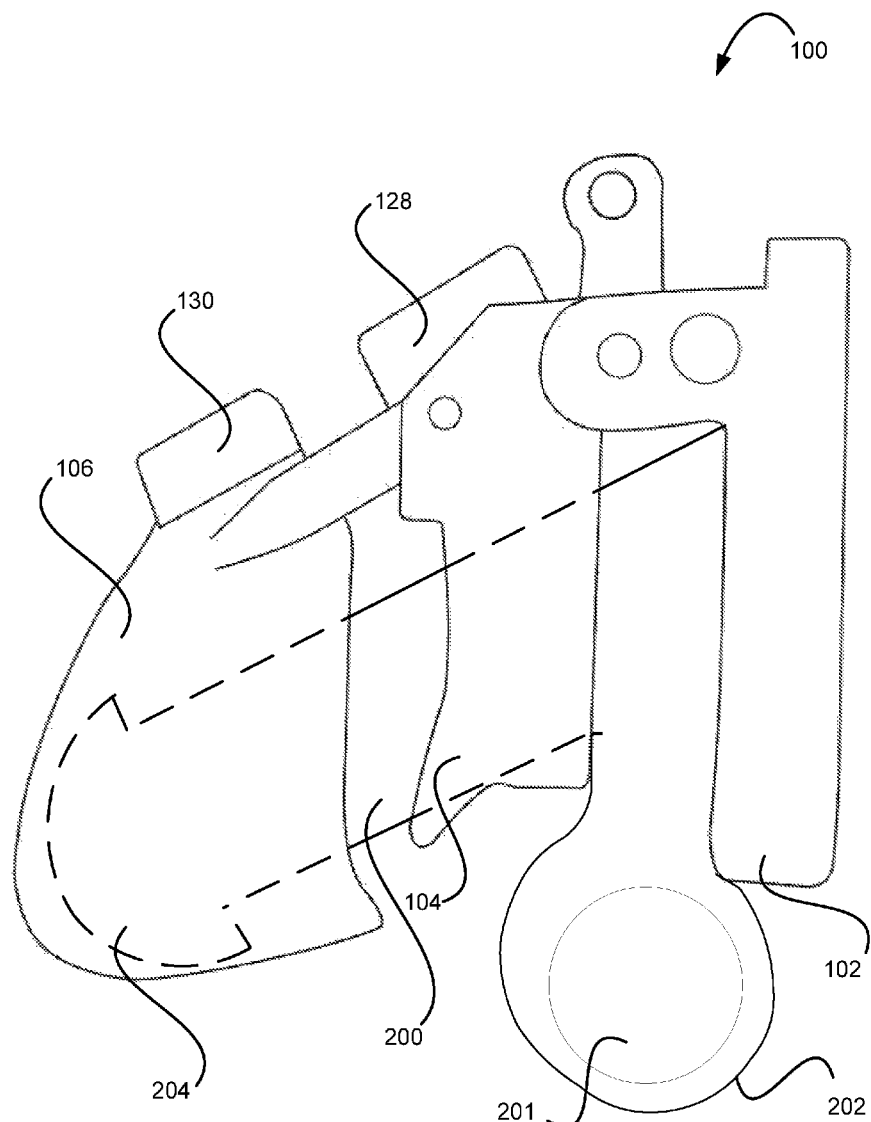
FIG. 5 is a side view of the device of the present invention, worn on a user's penis.

Referring now to the drawings, FIG. 1 is a perspective drawing illustrating a first loop, a second loop, and a cup of the device of the present invention detached from each other. FIG. 2 is a perspective drawing illustrating a device 100 of the present invention in an open mode. FIGS. 3 and 4 are perspective drawings illustrating a device of the present invention in a closed mode. FIG. 5 is a side view of the device of the present invention, worn on a user's penis.

As can be seen in FIG. 1, the device 100 includes a first loop 102, a second loop 104, and a cup 106. As illustrated by FIGS. 2-5, the first loop 102 and the second loop 104 are joined via a first hinging unit, and are thus rotatable with respect to each other. In a first variant, the second loop 104 is joined to the cup 106 via a second hinging unit, and is rotatable with respect to the cup 106. In a second variant, the second loop and the cup are fixedly joined to each other to form a housing, and may not be rotatable with respect to each other.

The first loop 102 is large enough to enable the passage of the penis shaft 200 and scrotum 202 and testicles 201 therethrough and is configured for being located behind the scrotum and encircling a base of the penis. In this manner, the testicles are located between the first loop and second loop when the device 100 is in its closed mode. Optionally, the second loop 104 is smaller than the first loop 102 and only enables passage of the penis shaft 200, but not of the scrotum 202. The cup 106 is a concave structure having an inner surface and an outer surface, and is configured for enclosing the penis head 204, or any section of the penis which includes the penis tip.

In an open mode of the device (FIG. 2), the penis and scrotum can be inserted through the first loop 102. The penis is then rotated upward to pass through second loop 104. Once this stage is reached, the device 100 can be manipulated as follows, in order to be arranged and locked in its closed mode. First, the second loop 104 (or the housing formed by the second loop and the cup) is rotated toward the first loop 102 until a distance D is present between the first and second loop (see FIG. 4). The distance D is selected to be small enough to keep the testicles 201 (see FIG. 5) in place and prevent the testicles from entering the gap between the first and second loop, while being large enough to prevent the first and second loops from applying too much pressure on the scrotum 202. Subsequently, if the cup and the second loop are hinged to each other, the cup 106 is rotated toward the second loop 104 in order to enclose the head of the penis (see FIG. 5). In this manner the device 100 is brought to its closed mode.

Next, a fixing mechanism is applied to the loops and the cup (see FIGS. 6 through 10) to prevent relative motion between the first loop and the second loop and, if the cup and the second loop are hinged to each other, relative rotation between the cup and the second loop. Finally, a locking mechanism is joined to the fixing mechanism to prevent removal of the fixing mechanism (see FIGS. 11 and 12).

In a closed mode of the device 100, a distance D is present between the first and second loop, to leave room for the testicles. It should be understood that the distance D is selected to be small enough to keep the testicles in place and prevent the testicles from entering the gap between the first and second loop, while being large enough to prevent the first and second loops from applying too much pressure on the scrotum 202. Thus, when locked in the closed mode of the device 100, the device cannot be easily removed from the user's penis, since the testicles cannot pass through the gap between the first and second loop, and this cannot reach and exit the first loop. Optionally, in the closed mode, a distance X is present between the second loop and the cup, so as to leave at least part of the penis exposed. This applies to the embodiment in which the cup and second loop are hinged to each other and to the embodiment in which the cup and second loop are fixedly joined to each other to form the housing. The distance X is chosen to be short enough to prevent the penis from exiting the cup, and long enough to prevent the cup from pressing too hard on the penis, and/or from rubbing on the excess skin around the penis if the penis is thick, and/or from rubbing on the foreskin. In the closed mode, the planes of the first and second loop substantially face each other, and the plane of the second loop faces the inner surface of the cup. For example, in the closed mode, the first loop 102 and the second loop 104 may substantially parallel to each other.

The second loop 104 is joined to a first tube 128. The first tube is outside the second loop 104 and extending at a non-zero angle with respect to the plane of the second loop. Optionally, the cup 106 is joined to a second tube 130. The second tube is joined to the outer surface of the cup 106. In a closed mode of the device 100, the first tube 128 is aligned with the second tube 130. As will be explained below, with reference to FIGS. 7-9, this enables a peg to traverse both tubes to prevent relative motion between the second loop 104 and the cup 106, if the cup and the second loop are hinged to each other.

Preferably, a slit or opening 132 is present at the tip of the cup. The slit or opening 132 enables urine to exit the cup's tip, while the cup encloses to the user's penis head. In this manner, the user is able to urinate comfortably while wearing the chastity device 100.

In some embodiments of the present invention, the first hinging unit joining the first loop 102 and the second loop 104 includes a first appendage 108, a second appendage 110, a third appendage 112, a fourth 114, a first pin 116, and a second pin 118. The first appendages 108 and the second appendage 110 are substantially parallel to each other, are fixed to the first loop 102, and extend away from a plane of the first loop 102. The third appendage 112 and the fourth appendage 114 are substantially parallel to each other, are fixed to the second loop 104, and extend away from a plane of the second loop 104. The first pin 116 traverses (and thus joins) the first appendage 108 and the third appendage 112 via their respective apertures 108b and 112b. The second pin 118 traverses (and thus joins) the second appendage 110 and the fourth appendage 114 via their respective first apertures 110b and 114b. The first and second pins are aligned to extend along the same axis, to enable relative rotation between the first loop and the second loop.

The pins traverse the respective appendages in a manner that allows relative rotation between the first and second loop. This may be achieved, for example, if the apertures 108b and 112b of the first and third appendages traversed by the first pin 116 and/or the apertures 110b and 114b of the second and fourth appendages traversed by the second pin 118 are larger than the cross sections of the respective pins. Moreover, if the pins have a smaller cross section than their respective apertures, some movement between the loops is allowed, enabling the device to adjust to motions of the penis.

According to a preferred embodiment, the apertures traversed by the first and second pin are substantially as large as the pins' cross section, the apertures are circular, and the pins are cylindrical. This configuration enables the relative rotation between the first loop 102 and the second loop 104. Moreover, the matching dimension of the pins and the holes increases the stability of the device, by limiting any motion between the first and second loop except for rotation around the pins.

The first appendage 108 has a first hole 108a, the second appendage 110 has a second hole 110a, the third appendage 112 has a third hole 112a, and the fourth appendage 114 has a fourth hole 114a. In a closed mode, the first hole 108a and the third hole 112a are aligned with each other, while the second hole 110a and the fourth hole 114a are aligned with each other. These alignments enable the insertion of pegs through these holes, to prevent the relative rotation of between the first loop and the second loop, as will be described below with reference to FIGS. 8-10.

In some embodiments of the present invention, a second hinging unit joins the second loop 104 and the cup 106, and includes a fifth appendage 120, a sixth appendage 122, a third pin 124, and fourth pin 126. The fifth appendage 120 and the sixth appendage 122 are joined to the cup, extend away from the cup, and are substantially parallel to each other. The third pin 124 traverses (and thus joins) the fifth appendage 120 and a section of the second loop 104 via their respective apertures 120a and 121. The fourth pin 126 traverses (and thus joins) the sixth appendage 122 and a section of the second loop 104 via their respective apertures 122a and 123. The third pin 124 and the fourth pin 126 are aligned to extend along a common axis. In this manner, relative rotation between the second loop 104 and the cup 106 is enabled. The third and fourth pins traverse the respective appendages and respective sections of the second loop in a manner that allows relative rotation between the cup and second loop.

Optionally, in a closed mode of the device 100, a bottom section of the fifth appendage 120 and a bottom section of the sixth appendage 122 touch the second loop 104. In this manner, further rotation of the cup and the second loop toward each other (e.g., counterclockwise rotation of the cup towards the second loop) is prevented.

In the figures, the loops 102 and 104 are ring shaped, while the cup is curved. It should be noted that this is not necessary. The loops may be oval, elliptical, or polygonal or any other shape, as long as passage of the penis and scrotum is enabled through the first loop 102, and the passage of the penis and optionally of the scrotum is enabled through the second loop 104. The inner and outer surface of the cup may also be of different shapes.

Moreover, the first hinging unit connecting the first loop and the second loop is shown to include two hinges: the first formed by the first appendage 108, the third appendage 112, and the first pin 116, and the second formed by the second appendage 110, the fourth appendage 114, and the second pin 118. This is not necessary, since a single hinge would be sufficient. Similarly, if present, the second hinging unit connecting the cup and the second loop is shown to include two hinges as well: one formed by the fifth appendage 120 and the third pin 124, and one formed by the sixth appendage 122 and the fourth pin 126. This is not necessary, since a single hinge would be sufficient.

Figure 6:
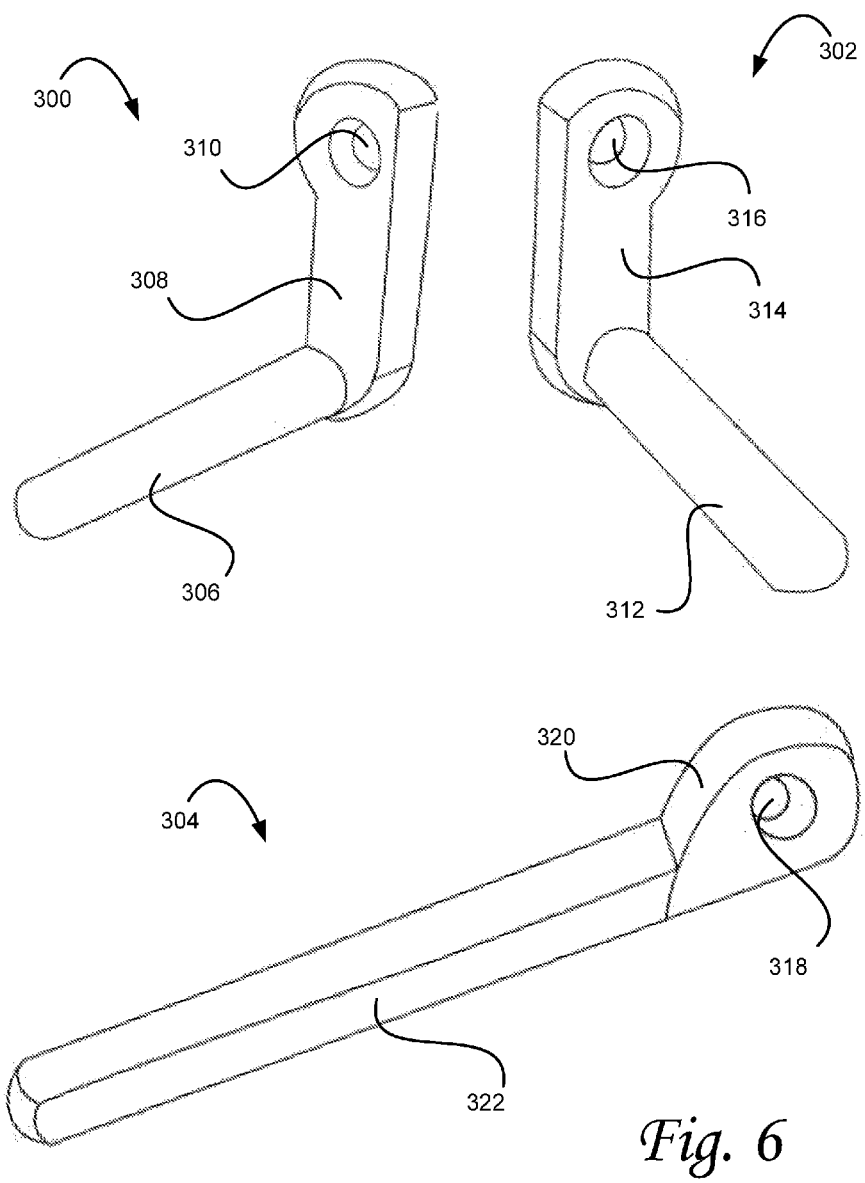
FIG. 6 is a perspective drawing illustrating the pegs of the device, according to some embodiments of the present invention.
Figure 7:
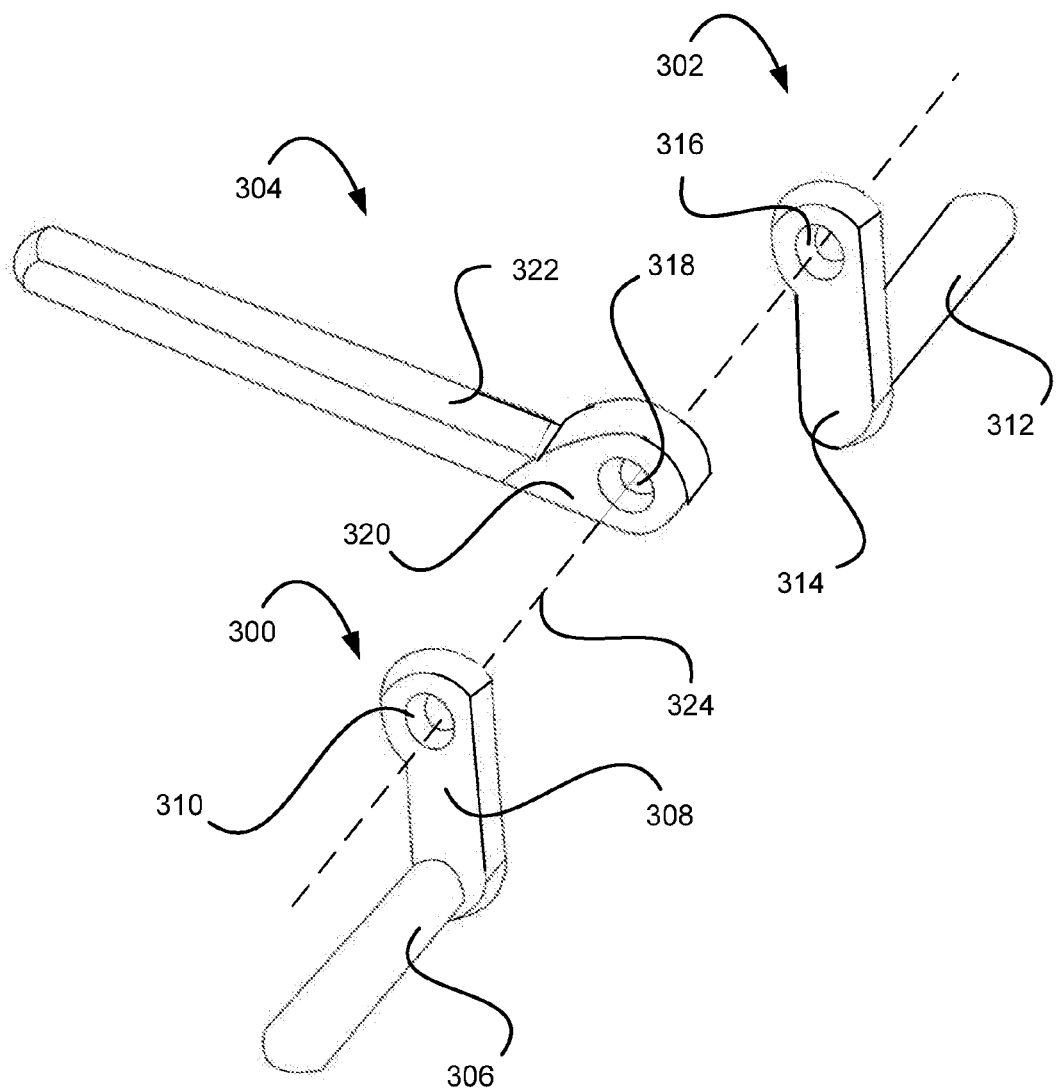
FIG. 7 is a perspective drawing illustrating the pegs of FIG. 6 when the pegs are aligned with each other.

Reference is now made to FIGS. 6 and 7, which are perspective drawing illustrating the pegs of the device, according to some embodiments of the present invention. In FIG. 6, the pegs are shown as independent elements. In FIG. 7, the pegs are shown to be aligned with each other.

The above described device 100 includes a mechanism for fixing the device into its closed mode. A first part of the mechanism is configured to fix the positions of the first and second loop relative to each other. A second part of the mechanism is configured to fix the positions of the second loop and cup relative to each other.

In some embodiments of the present invention the fixing mechanism is in the form of pegs: two two-part pegs 300 and 302, and optionally a straight peg 304. The first two-part peg 300 includes a first rod 306 and a first bar 308 at a non-zero angle with the first rod 306. Optionally, the first rod and the first bar are substantially perpendicular to each other. The first bar 308 has a first orifice 310, which has a central axis substantially parallel to the first bar.

Similarly, the second two-part peg 302 includes a second rod 312 and a second bar 314 at a non-zero angle with the second rod 312. Optionally, the second rod and the second bar are substantially perpendicular to each other. The second bar 314 has a second orifice 316, which has a central axis substantially parallel to the second bar.

The straight peg 304 is a straight shaft having a third orifice 318. Optionally, the bar section 320 with the third orifice 318 is larger than the rod section 322 without the orifice 318.

As can be seen in FIG. 7, the geometries of the pegs 300, 302, and 304 enable the pegs to be aligned with each other. In the aligned configuration, the orifices 310, 316, and 318 are set along (traversed by) the same axis 324. The straight peg 304 (if present) is located between the first peg 300 and the second peg 302. The first rod 306 and the second rod 312 are set to point away from each other (and may be optionally, but not necessarily set along the same line). The rod section 322 is perpendicular to the first and second rod.

Optionally, the first bar 308, the second bar 314, and the bar section 320 have flat side surfaces. When the pegs 300, 302, and 304 are aligned, the flat surfaces are parallel to each other and the first bar 308, the second bar 314, and the bar section 320 may be therefore be set alongside each other.

Figure 8:
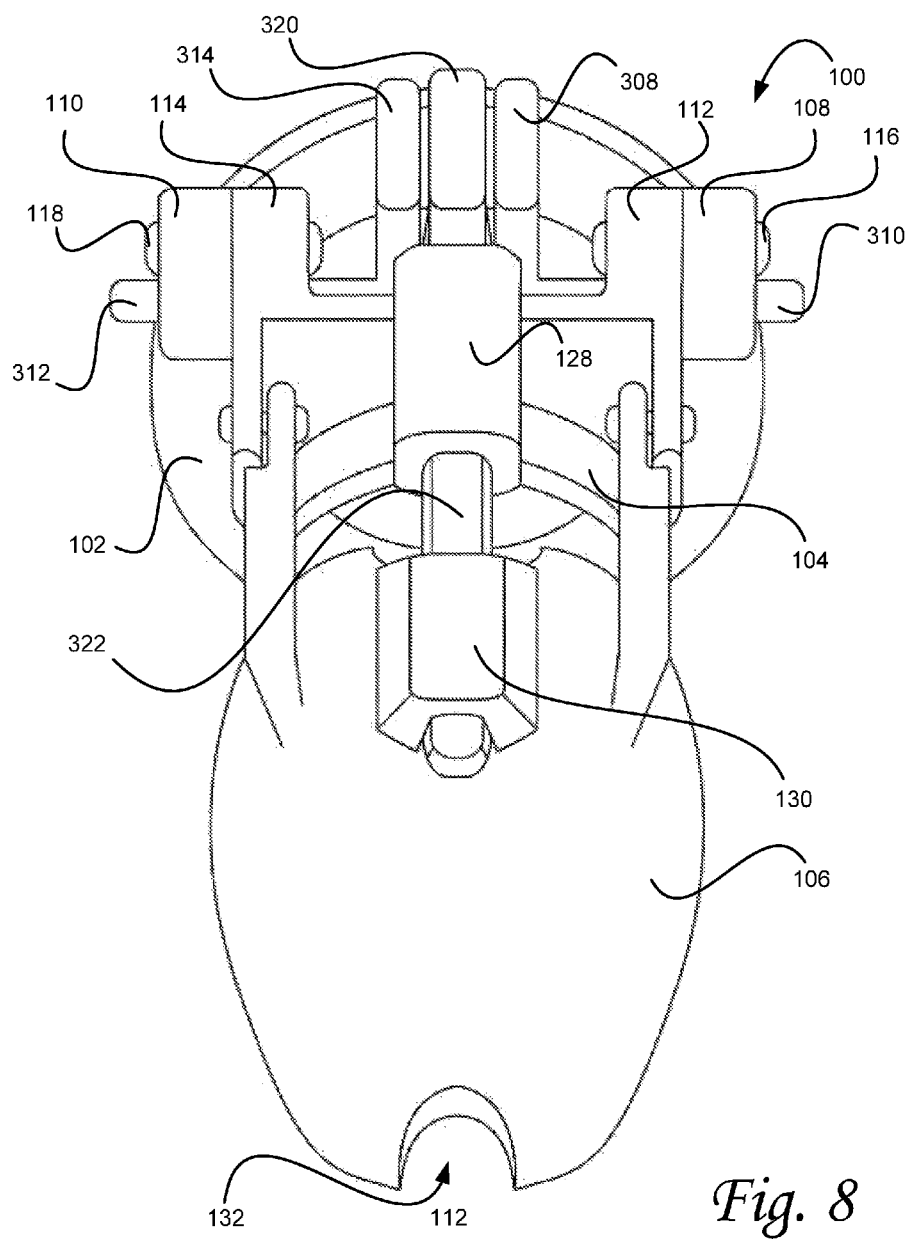
FIGS. 8 to 10 are drawings illustrating the device of the present invention in a closed mode after insertion of the pegs.
Figure 9:
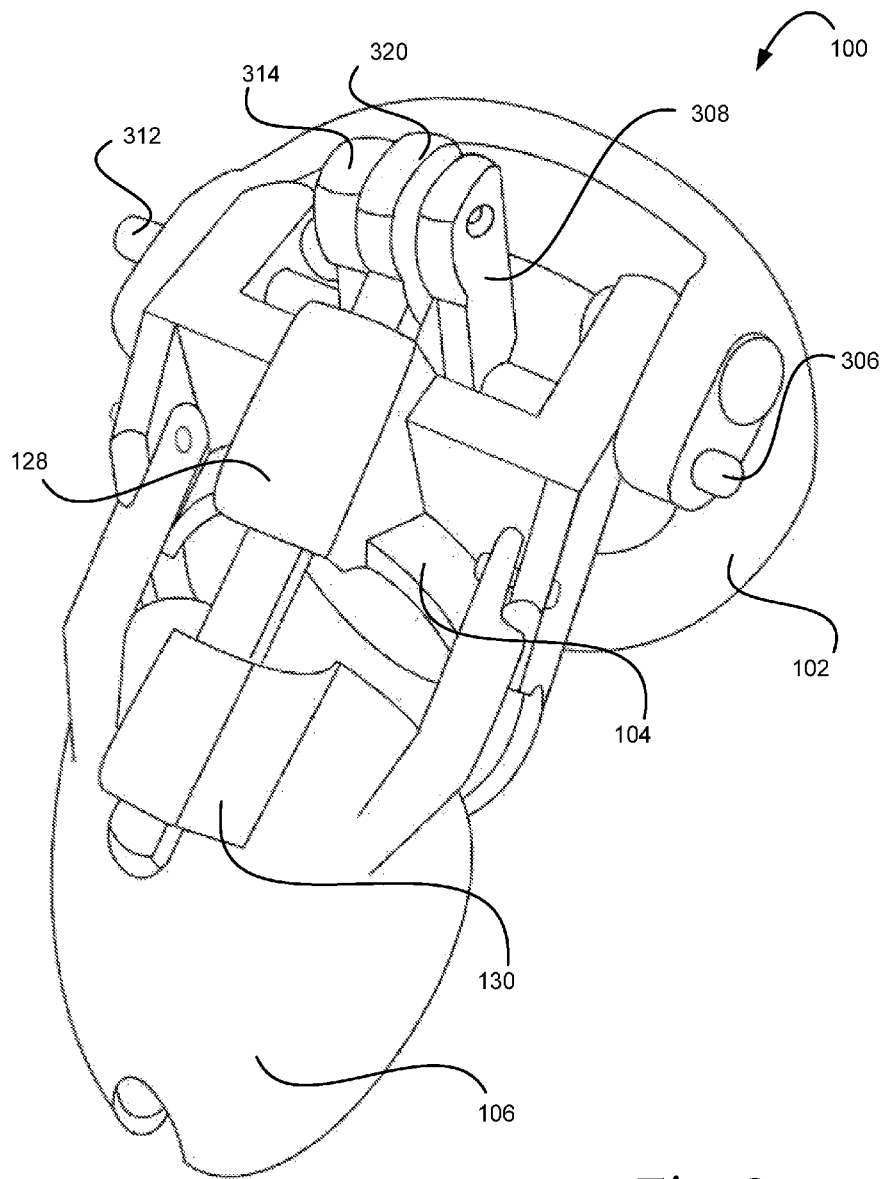
Figure 10:
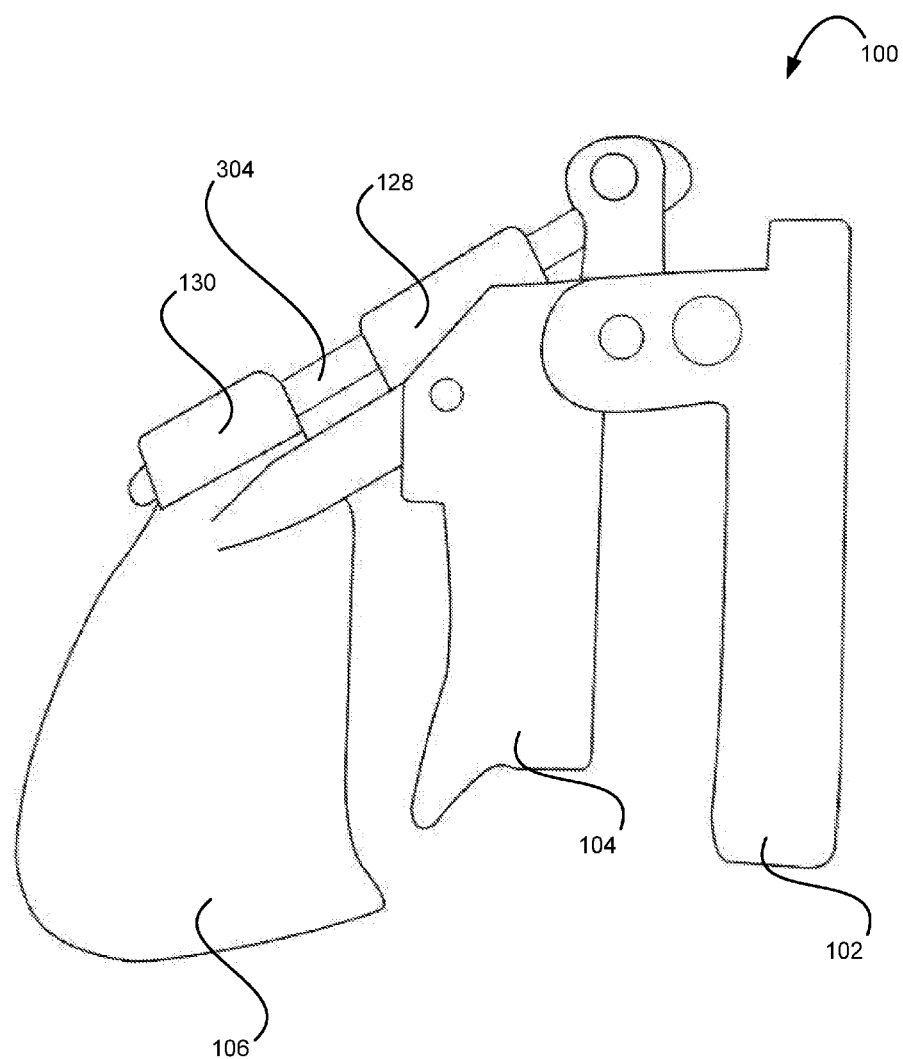

Reference is now made to FIGS. 8 to 10, which are drawings illustrating the device 100 of the present invention in a closed mode after insertion of the pegs.

As mentioned above, with reference to FIGS. 1-5, when the is device 100 is in its closed mode, the hole 108a of the first appendage 108 and the hole 112a of the third appendage 112 are aligned. When the first rod 306 of the first peg 300 is inserted into the holes 108a and 112a, the first appendage 108 and the third appendage 112 are joined at two locations (by the first pin 116 and by the first two-part peg 300). In this manner, motion between the first appendage 108 and the third appendage 112 is substantially prevented, thereby fixing the relative position between the first loop 102 and the second loop 104. Optionally, in order to strengthen the link between the first and second loops 102 and 104, the second rod 312 of the second peg 302 is set to traverse the second appendage 110 and the fourth appendage 114 via their respective holes.

In the embodiment in which the second loop and the cup are rotatable with respect to each other, the straight peg 304 is present and is configured for traversing the first tube 128 joined to the second loop 104 and for pressing on an outer surface of the cup 106 to prevent a rotation of the cup about the pins 124 and 126. Optionally, if the second tube 130 is present, the straight peg 304 traverses the second tube 130 as well. Thus, relative motion between the second loop 104 and the cup is prevented.

Thus, the first two-part peg 300 (and optionally the second two-part peg 302) forms the section of the fixing mechanism, which fixes the position of the first loop 102 relative to the second loop 104. In the embodiment in which the second loop and the cup are rotatable with respect to each other, the straight peg 304 forms the section of the fixing mechanism which fixes the position of the cup 106 relative to the second loop 104.

It should be noted that a single straight peg is shown to fix the cup and the second loop. It is within the scope of the present invention to have two or more straight pegs, each traversing a respective tube joined to the second loop (and optionally also a respective tube joined to the cup).

The cross section of the rods 306 and 312 and of the rod section 322 may be of any shape, for example, round, oval, or polygonal. Moreover, the two pegs are used for fixing the positions of the first and second loops with respect to each other. One peg traversing the first appendage 108 and the third appendage 112 may be used instead. Alternatively, a single long peg traversing the first, second, third, and fourth appendages 108, 110, 112, and 114 may be used as well.

Figure 11:
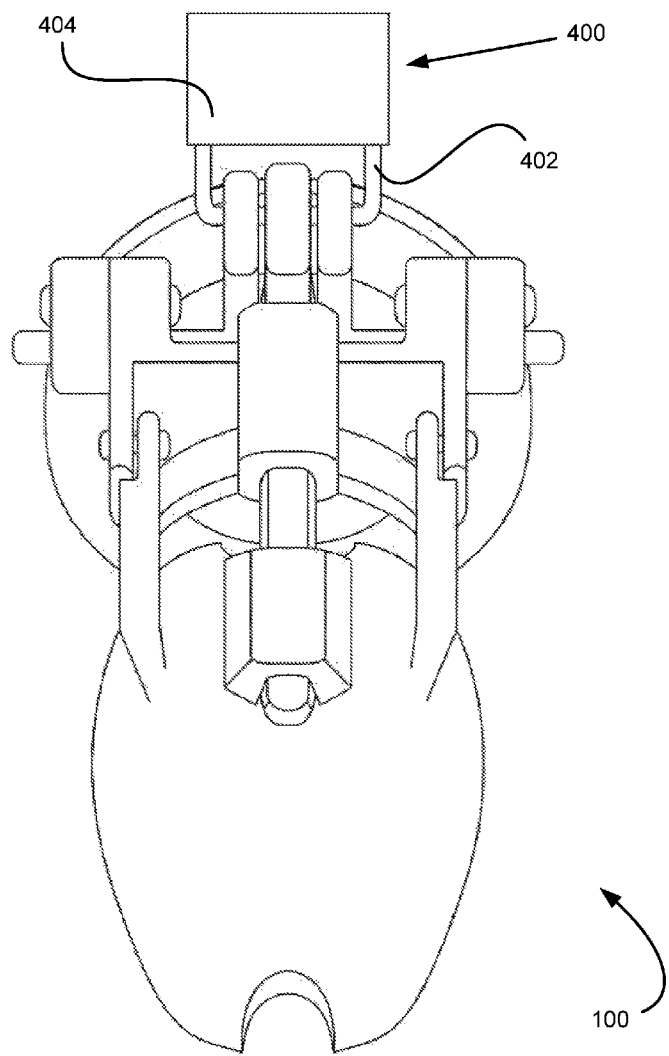
FIGS. 11 and 12 are drawings illustrating the device of the present invention in a locked mode.
Figure 12:
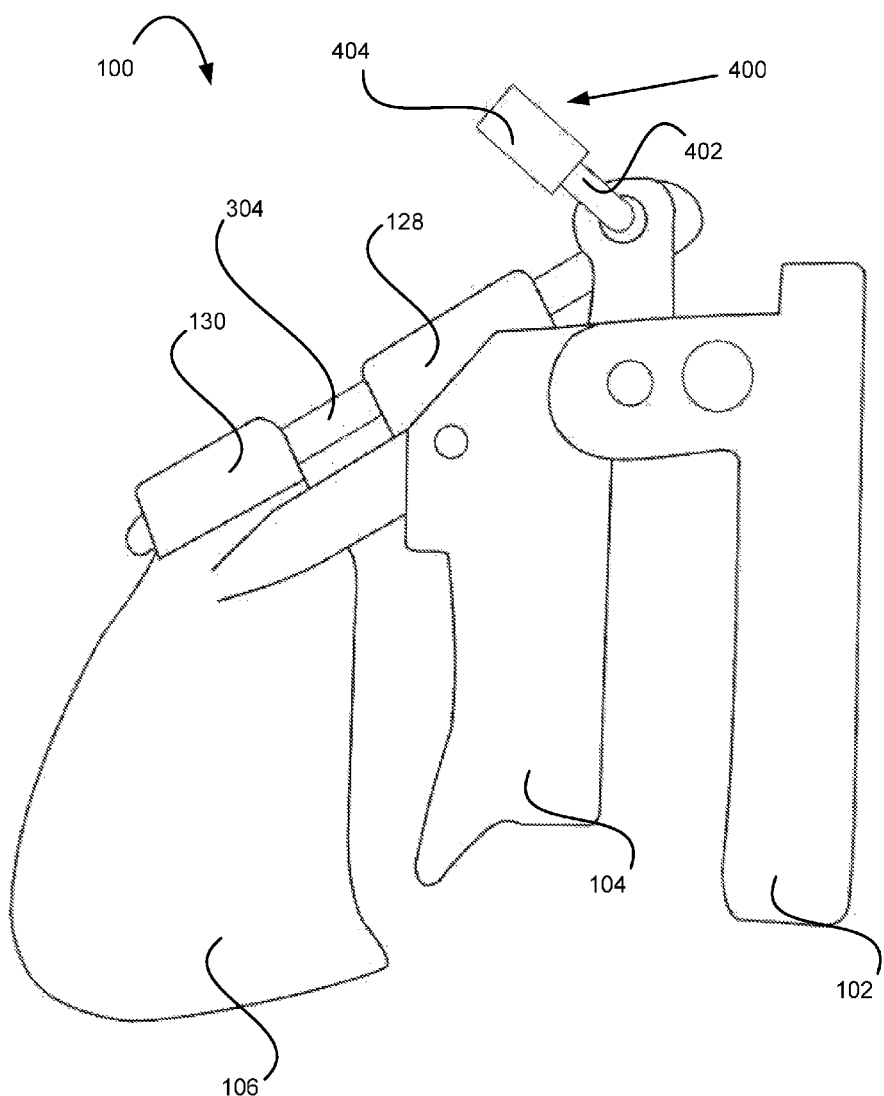

Reference is now made to FIGS. 11 and 12, which are drawings illustrating the device 100 of the present invention in a locked mode.

After fixing the device 100 in its closed mode, as explained above, the device 100 can be locked, to prevent a user from removing the device from the user's penis. Optionally, the bars 308 and 314 of the first and second pegs are set abreast of each other, and the respective orifices 310 and 316, are aligned, as seen in FIG. 7. This enables a shackle 402 of a padlock 400 to traverse the bars 308 and 314. The shackle 402 is locked to the body 404 of the padlock 400. The locking prevents the user from removing the pegs 300 and 302, and therefore the device 100 is securely locked in it is closed mode. In the embodiment in which the second loop and the cup are rotatable with respect to each other, the straight peg 304 is also present, and the bar section 320 is set abreast of the bars 308 and 314 of the first and second pegs, such that the orifices 310, 316, and 318 are aligned, as seen in FIG. 7, and traversable by the shackle of the padlock. In this manner, the user is further prevented from removing the straight peg 304, ensuring that the device 100 is securely locked in it is closed mode. In the closed mode, a section of the penis which includes the penis' tip is enclosed by the cup, to prevent the user from using his penis for sexual acts. The padlock may be unlocked and removed by a person holding the padlock's key.

As mentioned above, according to some embodiments of the present invention, only the first loop and the second loop are joined by a single hinge. In such case, the first peg 300 is configured for preventing the relative rotation between the first loop and the second loop, while the second peg 302 is not present. In this case, the straight peg 304 is present and inserted into the first tube 128, even if the cup and the second loop are not rotatable with respect to each other. The presence of the straight peg enables the shackle of the padlock to lock the fixing mechanism by traversing the bar section 320 and the first bar 308 via their respective orifices 318 and 310, in order to prevent removal of the first peg 300.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:
1. A male chastity device, comprising:
a first loop, configured to allow passage of a penis and scrotum of a user, and for encircling to encircle the penis behind the scrotum;
a second loop, configured to allow passage by at least the penis, and to encircle the penis ahead of the scrotum, so that the user's testicles are located between the first loop and second loop;
a cup, joined to the second loop and configured to enclose at least a head of the penis;

a first hinging unit, joining the first loop to the second loop, enables the first and the second loop to rotate with respect to each other, wherein the first hinge unit further comprises:
- a first appendage joined to the first loop and extending away from a plane of the first loop, the first appendage having a first aperture;
- a second appendage joined to the second loop and extending away from a plane of the second loop, the second appendage having a second aperture; and
- a first pin configured for traversing to traverse the first and second apertures, thereby joining the first loop and the second loop, while enabling the first and second loop to rotate with respect to each other about the first pin; and a removable fixing mechanism, configured to be removably joined to the device and, when joined to the device, to prevent removal of the device from the penis by limiting or blocking relative rotation between the first loop and the second loop.

2. The device of claim 1, wherein the cup and the second loop are not movable with respect to each other.

3. The device of claim 1, wherein:
the cup and the second loop are rotatable with respect to each other;
the device comprises a second hinging unit, joining the second loop to the cup, and enables the cup and second loop to rotate with respect to each other; and
the removable fixing mechanism, when joined to the device, is configured to prevent removal of the device from the penis by limiting or blocking relative rotation between the first loop and the second loop, and by limiting or blocking relative rotation between the cup and the second loop.

4. The device of claim 3, wherein the second loop has a fifth aperture, and the second hinging unit comprises:
- a fifth appendage joined to the cup, extending away from the cup on the cup's concave side, and having a sixth aperture; and
- a third pin configured to traverse the fifth aperture and the sixth aperture thereby joining the cup and the second loop, while enabling the cup and second loop to rotate with respect to each other.

5. The device of claim 4, wherein the second loop has a seventh aperture and the second hinging unit further comprises:
- a sixth appendage joined to the cup, extending away from the cup on the cup's concave side, and having an eighth aperture; and
- a fourth pin configured to traverse the seventh and eighth apertures thereby joining the cup and the second loop;
- wherein the fifth, sixth, seventh, and eighth apertures are aligned along a second axis when the cup and the second loop are joined, such that the third and fourth pins are aligned to extend along the second axis, thereby enabling the cup and the second loop to rotate with respect to each other.

6. The device of claim 3, comprising a first tube joined to the second loop, wherein the fixing mechanism comprises a third peg configured to traverse the first tube and for pressing on an outer surface of the cup to prevent the relative rotation between the cup and second loop.

7. The device of claim 6, comprising a second tube joined to the outer surface of the cup, wherein the third peg is configured to traverse the first tube and the second tube when the first and second tubes are aligned with each other, thereby to prevent the relative rotation between the cup and second loop.

8. The device of claim 1, further comprising a removable locking mechanism, configured to be removably joined to the fixing mechanism to prevent a removal of the fixing mechanism from the device, and removed from the fixing mechanism to enable a removal of the fixing mechanism from the device.

9. The device of claim 1, wherein the first hinging unit further comprises:
- a third appendage joined to the first loop and extending away from a plane of the first loop, the third appendage being substantially parallel to the first appendage and having a third aperture;
- a fourth appendage joined to the second loop and extending away from a plane of the second loop, the fourth appendage having a fourth aperture; and
- a second pin configured to traverse the third and fourth apertures, thereby joining the first loop and the second loop;
- wherein the first, second, third, and fourth apertures are aligned along a first axis when the first and second loops are joined, such that the first and second pins are aligned to extend along the first axis, thereby enabling the first and second loop to rotate with respect to each other.

10. The device of claim 9, wherein:
the first appendage has a first hole and the second appendage has a second hole;
the third appendage has a third hole and the fourth appendage has a fourth hole; and
the fixing mechanism comprises:
- a first peg configured to traverse the first and second holes when the first and second holes are aligned with each other, thereby limiting the relative rotation between the first loop and the second loop about the first pin; and
- a second peg configured to traverse the third and fourth holes when the third and fourth holes are aligned with each other, thereby limiting the relative rotation between the first loop and the second loop about the second pin.

11. The device of claim 10, wherein:
the first peg comprises:
- a first rod configured to traverse the first and second holes; and
- a first bar joined to the first rod and oriented at a non-zero angle with respect to the first rod, the first bar having a first orifice;
the second peg comprises:
- a second rod configured to traverse the third and fourth holes; and
- a second bar joined to the second rod and oriented at a non-zero angle with respect to the second rod, the second bar having a second orifice;
the device is configured such that the first orifice and the second orifice are aligned along a third axis when the first peg traverses in the first and second holes, the second peg traverses the third and fourth holes.

12. The device of claim 11, further comprising a padlock having a shackle and a body, wherein the shackle is configured to traverse the first and second orifices when the first and second orifices are aligned along the third axis and for being locked to the body, to prevent a removal of the first and second pegs, thereby preventing removal of the fixing mechanism and removal of the device from the penis.

13. The device of claim 10, comprising a first tube joined to the second loop, wherein:
the cup and the second loop are rotatable with respect to each other;
the device comprises a second hinging unit, joining the second loop to the cup, and enables the cup and second loop to rotate with respect to each other;
the removable fixing mechanism, when joined to the device, is configured to prevent removal of the device from the penis by limiting or blocking relative rotation between the first loop and the second loop, and by limiting or blocking relative rotation between the cup and the second loop;
the fixing mechanism further comprises a third peg configured to traverse the first tube and to press on an outer surface of the cup to prevent the relative rotation between the cup and second loop;
the first peg comprises:
  a first rod configured to traverse the first and second holes; and
  a first bar joined to the first rod and oriented at a non-zero angle with respect to the first rod, the first bar having a first orifice;
the second peg comprises:
  a second rod configured to traverse the third and fourth holes; and
  a second bar joined to the second rod and oriented at a non-zero angle with respect to the second rod, the second bar having a second orifice;
the third peg has a third orifice;
the device is configured such that the first orifice, the second orifice, and the third orifice are aligned along a third axis when the first peg traverses the first and second holes, the second peg traverses the third and fourth holes, and the third peg traverses the first tube and presses on the cup's outer surface.

14. The device of claim 13, further comprising a padlock having a shackle and a body, wherein the shackle is configured to traverse the first, second, and third orifices when the first, second, and third orifices are aligned along the third axis and to be locked to the body, to prevent a removal of the first, second, and third pegs, thereby preventing removal of the fixing mechanism and removal of the device from the penis.

15. The device of claim 1, wherein:
the first appendage has a first hole and the second appendage has a second hole; and
the fixing mechanism comprises a first peg configured to traverse the first and second holes when the first and second holes are aligned with each other, thereby limiting the relative rotation between the first loop and the second loop about the first pin.

16. The device of claim 15, comprising a first tube joined to the second loop, wherein:
the cup and the second loop are rotatable with respect to each other;
the device comprises a second hinging unit, joining the second loop to the cup, and enables the cup and second loop to rotate with respect to each other;
the removable fixing mechanism, when joined to the device, is configured to prevent removal of the device from the penis by limiting or blocking relative rotation between the first loop and the second loop, and by limiting or blocking relative rotation between the cup and the second loop;
the fixing mechanism further comprises a third peg configured to traverse the first tube and for pressing to press on an outer surface of the cup to prevent the relative rotation between the cup and second loop;
the first peg comprises:
  a first rod configured to traverse the first and second holes; and
  a first bar joined to the first rod and oriented at a non-zero angle with respect to the first rod, the first bar having a first orifice;
the third peg has a third orifice;
the device is configured such that the first orifice and the third orifice are aligned along a third axis when the first peg traverses the first and second holes and the third peg traverses the first tube and presses on the cup's outer surface.

17. The device of claim 16, further comprising a padlock having a shackle and a body, wherein the shackle is configured to traverse the first and third orifices when the first and third orifices are aligned along the third axis and for being locked to the body, to prevent a removal of the first and third pegs, thereby preventing removal of the fixing mechanism and removal of the device from the penis.

* * * * *